United States Patent
He et al.

(10) Patent No.: US 10,398,457 B2
(45) Date of Patent: *Sep. 3, 2019

(54) LAPAROSCOPIC GALLBLADDER EXTRACTION DEVICE

(71) Applicants: The Regents of the University of Michigan, University of Michigan, Ann Arbor, MI (US); Covidien LP, Mansfield, MA (US)

(72) Inventors: Yuhao He, Beijing (CN); Scott LaTulip, Canton, MI (US); Zongchang Liu, Shandong (CN); Yang Wei, Ann Arbor, MI (US); Taiming Chu, Shanghai (CN)

(73) Assignees: Covidien LP, Mansfield, MA (US); The Regents of the University of Michigan, Ann Arbor, MI (US)

( * ) Notice: Subject to any disclaimer, the term of this patent is extended or adjusted under 35 U.S.C. 154(b) by 296 days.

This patent is subject to a terminal disclaimer.

(21) Appl. No.: 15/640,636

(22) Filed: Jul. 3, 2017

(65) Prior Publication Data

US 2017/0296211 A1    Oct. 19, 2017

Related U.S. Application Data

(63) Continuation of application No. 13/956,754, filed on Aug. 1, 2013, now Pat. No. 9,693,790.

(Continued)

(51) Int. Cl.
*A61B 17/22* (2006.01)
*A61B 17/295* (2006.01)

(Continued)

(52) U.S. Cl.
CPC ...... *A61B 17/22031* (2013.01); *A61B 17/295* (2013.01); *A61B 2017/00287* (2013.01); *A61B 2017/2926* (2013.01)

(58) Field of Classification Search
CPC . A61B 17/22031; A61B 17/295; A61B 17/29; A61B 17/22032; A61B 17/221; A61B 17/28; A61B 17/2812; A61B 17/282; A61B 17/285; A61B 17/26; A61B 17/2804; A61B 10/06; A61B 10/02;
(Continued)

(56) References Cited

U.S. PATENT DOCUMENTS

30,471 A    10/1860   Dudley
686,578 A   11/1901   Bowersox
(Continued)

*Primary Examiner* — Katherine H Schwiker (57) ABSTRACT

A surgical instrument for removing a gallbladder is provided. The surgical instrument includes a handle assembly, an elongated body portion extending distally from the handle assembly, and a capture portion operably mounted on a distal end of the elongated body portion. The capture portion defines a tissue receiving opening when in an open configuration and is configured for receipt through an incision when in the capture portion is in a closed configuration. The capture portion includes at least one sharpened member for cutting tissue received within the tissue receiving opening as the capture portion moves from the open configuration to the closed configuration. Also provided is a method of removing a gallbladder using a surgical instrument.

15 Claims, 8 Drawing Sheets

Related U.S. Application Data (60) Provisional application No. 61/679,036, filed on Aug. 2, 2012.

(51) Int. Cl.
*A61B 17/00* (2006.01)
*A61B 17/29* (2006.01)

(58) Field of Classification Search
CPC ........ A61B 2010/0208; A61B 18/1445; A61B 18/1447; A61B 2018/145; A61B 2018/1452; A61B 2018/1455; A61B 2018/1457; A61B 2017/2926; A61B 2017/2932; A61B 2017/2939; A61B 2017/294; A61B 2017/2947; A61B 2017/2944; A61B 2017/2933; A61B 2017/2934; A61B 2017/2936; A61B 2017/2937; A61B 2017/2938; A61B 2017/22034; A61B 2017/22035; A61B 2017/2948; A61B 2017/2906; A61B 2017/2908
USPC .................................................. 606/205–209
See application file for complete search history.

(56) References Cited

U.S. PATENT DOCUMENTS

| | | | |
|---|---|---|---|
| 3,895,636 A | | 7/1975 | Schmidt |
| 4,611,594 A | | 9/1986 | Grayhack et al. |
| 4,721,116 A | * | 1/1988 | Schintgen ............... A61B 10/02 600/564 |
| 4,741,335 A | | 5/1988 | Okada |
| 4,768,505 A | | 9/1988 | Okada et al. |
| 5,235,966 A | | 8/1993 | Jamner |
| 5,238,002 A | * | 8/1993 | Devlin ................... A61B 10/06 600/564 |
| 5,320,627 A | | 6/1994 | Sorensen et al. |
| 5,370,647 A | | 12/1994 | Graber et al. |
| 5,373,854 A | | 12/1994 | Kolozsi |
| 5,383,877 A | * | 1/1995 | Clarke ............... A61B 17/0469 606/139 |
| 5,535,754 A | * | 7/1996 | Doherty ................. A61B 10/06 600/564 |
| 5,755,661 A | | 5/1998 | Schwartzman |
| 5,776,075 A | | 7/1998 | Palmer |
| 5,788,710 A | | 8/1998 | Bates et al. |
| 5,797,958 A | | 8/1998 | Yoon |
| 5,984,939 A | * | 11/1999 | Yoon ................ A61B 17/12013 606/139 |
| 6,102,909 A | | 8/2000 | Chen et al. |
| 6,152,932 A | | 11/2000 | Ternstrom |
| 6,156,043 A | | 12/2000 | Krahn |
| 6,183,482 B1 | | 2/2001 | Bates et al. |
| 6,203,552 B1 | | 3/2001 | Bagley et al. |
| 6,238,414 B1 | | 5/2001 | Griffiths |
| 6,280,450 B1 | | 8/2001 | McGuckin, Jr. |
| 6,319,262 B1 | | 11/2001 | Bates et al. |
| 6,416,519 B1 | | 7/2002 | VanDusseldorp |
| 6,582,451 B1 | | 6/2003 | Marucci et al. |
| 6,679,893 B1 | | 1/2004 | Tran |
| 6,958,069 B2 | | 10/2005 | Shipp et al. |
| D583,941 S | | 12/2008 | Leroy |
| 8,308,738 B2 | * | 11/2012 | Nobis ..................... A61B 17/29 606/113 |
| 8,568,443 B1 | | 10/2013 | Jackman et al. |
| 9,693,790 B2 | | 7/2017 | He et al. |
| 2002/0123761 A1 | | 9/2002 | Barbut et al. |
| 2002/0137988 A1 | | 9/2002 | Shipp et al. |
| 2004/0215212 A1 | | 10/2004 | Teague et al. |
| 2005/0054946 A1 | * | 3/2005 | Krzyzanowski ........ A61B 10/06 600/564 |
| 2005/0090817 A1 | | 4/2005 | Phan |
| 2005/0222586 A1 | | 10/2005 | VanDusseldorp |
| 2006/0025781 A1 | | 2/2006 | Young et al. |
| 2006/0258954 A1 | * | 11/2006 | Timberlake ........... A61B 10/06 600/564 |
| 2008/0234725 A1 | | 9/2008 | Griffiths et al. |
| 2010/0152609 A1 | | 6/2010 | Zwolinski et al. |
| 2010/0204711 A1 | | 8/2010 | Kear et al. |
| 2011/0066158 A1 | | 3/2011 | Teague et al. |
| 2011/0066159 A1 | | 3/2011 | Teague et al. |
| 2011/0288579 A1 | | 11/2011 | Hyodo |

* cited by examiner

LAPAROSCOPIC GALLBLADDER EXTRACTION DEVICE

CROSS-REFERENCE TO RELATED APPLICATION

The application is a Continuation of U.S. patent application Ser. No. 13/956,754 filed Aug. 1, 2013, which claims benefit of and priority to U.S. Provisional Application No. 61/679,036, filed Aug. 2, 2012, the content of which is incorporated herein by reference in its entirety.

BACKGROUND

Technical Field

The present disclosure relates to instruments and methods for the removal of a gallbladder. More specifically, the present disclosure relates to a laparoscopic instrument for use in the removal of a gallbladder.

Background of Related Art

Laparoscopic cholecystectomy is the most commonly performed minimally invasive surgical procedure with over 500,000 surgeries performed annually in the U.S. alone. During a laparoscopic cholecystectomy procedure, after detachment, the gallbladder is removed through a trocar incision. To prevent bile from leaking from the gallbladder, the detached gallbladder is typically placed in a retrieval bag. When retrieval bags are unavailable, surgical teams may create a substitute using a latex glove. If a surgeon is unsuccessful at removing the gallbladder from the incision laparoscopically, the surgeon may often have to enlarge the incision with a scalpel, extract the bile out of the gallbladder using a syringe, and/or use clamps to pull the gallbladder out piece by piece. Gallbladders that are full of bile and/or stones and/or are too large to be easily pulled out through a laparoscopic incision make require as much as an additional 5-30 minutes of the surgical team's time. Extra time may also be required to clean up any spills. Caution is usually taken to prevent rupturing of the gallbladder upon extraction because bile and gallstones are toxic to internal tissue if not properly cleaned.

Therefore, during laparoscopic cholecystectomies there is a need for a time-efficient method that allows surgeons to remove the detached gallbladder through an incision in the abdominal wall created for a trocar without spilling any bile and/or stones from the gallbladder.

SUMMARY

Accordingly, a surgical instrument for removing a gallbladder is provided. The surgical instrument includes a handle assembly, an elongated body portion extending distally from the handle assembly, and a capture portion operably mounted on a distal end of the elongated body portion. The capture portion defines a tissue receiving opening when in an open configuration and is configured for receipt through an incision when in the capture portion is in a closed configuration. The capture portion includes at least one sharpened member for cutting tissue received within the tissue receiving opening as the capture portion moves from the open configuration to the closed configuration.

In one embodiment, the tissue capture portion includes a plurality of capture sections. The plurality of capture sections may form a longitudinal cylinder when the capture portion is in a closed configuration. Each of the capture sections may be operably connected to a linkage system for moving the capture sections between the closed configuration and the open configurations. Each linkage assembly may include a proximal linkage member and a distal linkage member. Each of the proximal and distal linkage members may be operably connected to an inner shaft. The at least one sharpened member may be formed on the distal linkage member. The handle assembly may include a trigger for closing the capture portion. The handle assembly may include a release member for opening the capture portion. The elongated body portion may include an inner shaft and an outer shaft.

Also provided is a method of removing tissue from within a body cavity. The method includes a step of providing a surgical instrument including a capture portion operably mounted on a distal end of an elongated body portion. The capture portion defines a tissue receiving opening when in an open configuration and being configured for receipt through an incision when in a closed configuration. The capture portion may include at least one sharpened member for cutting tissue received within the tissue receiving opening as the capture portion moves from the open configuration to the closed configuration. The method further includes the steps of inserting the capture portion of the surgical instrument through an incision, positioning tissue within the tissue receiving opening of the capture portion, placing a retrieval bag about the capture portion of the surgical instrument, moving the capture portion from the open configuration to the closed configuration to cause the engagement of the sharpened member with the tissue, and removing the capture portion through the incision.

In one embodiment, the step of receiving the capture portion of the surgical instrument through the incision is performed when the capture portion is in the closed configuration. The step of placing the retrieval bag about the capture portion of the surgical instrument may include sealing the retrieval bag about the capture portion to prevent leakage. In addition, the step of inserting the capture portion of the surgical instrument through an incision may be facilitated through the use of an access port.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein.

DETAILED DESCRIPTION

Embodiments of the presently disclosed surgical instrument in accordance with the present disclosure will now be described in detail with reference to the drawings wherein like reference numerals identify similar or identical structural elements. As used herein, as is traditional, the term "proximal" refers to the end of the instrument which is closer to the user and the term distal refers to the end of the instrument which is further away from the user.

Figure 1:
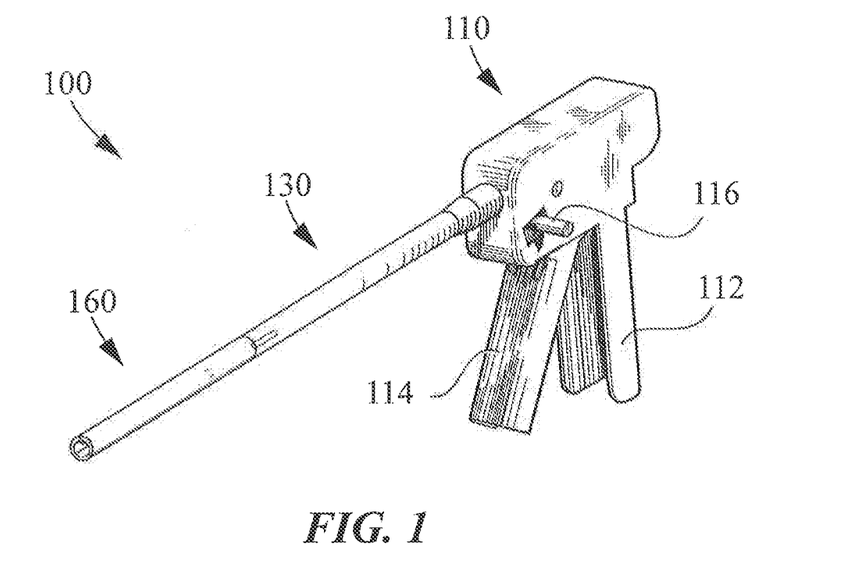
FIG. 1 is a perspective view of a surgical instrument in accordance with an embodiment of the present disclosure, with a capture portion in a first or closed condition.
Figure 2:
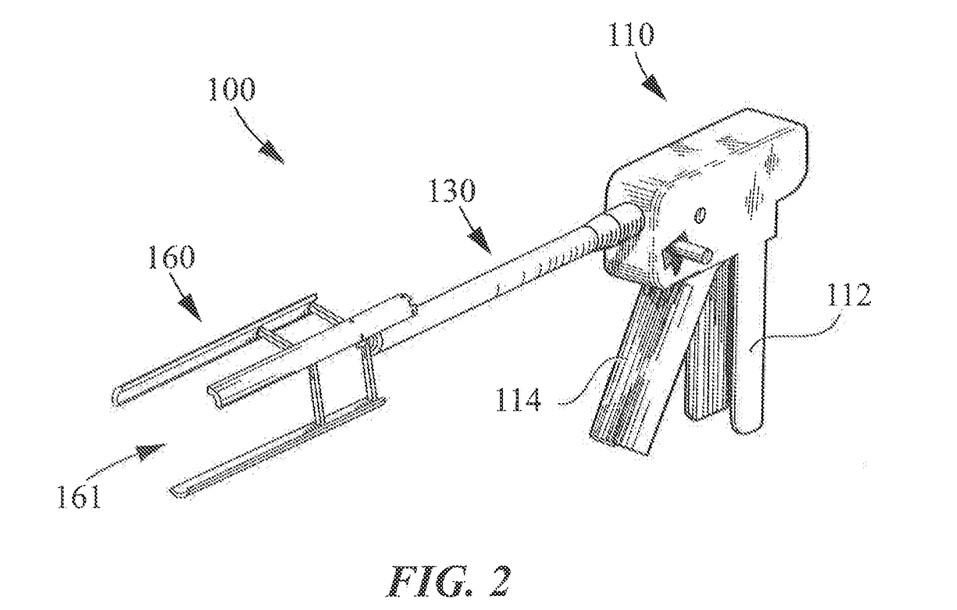
FIG. 2 is a perspective view of the surgical instrument of FIG. 1, with the capture portion in a second or open condition.

FIGS. 1-6 illustrate an embodiment of the presently disclosed instrument for use in laparoscopic cholecystectomies and is shown generally as surgical instrument 100. With reference to FIGS. 1 and 2, surgical instrument 100 includes a handle assembly 110, an elongated body 130 extending distally from handle assembly 110, and a capture portion 160 operably mounted on a distal end of elongated body 130. As will be discussed in further detail below, elongated body 130 and capture portion 160 of surgical instrument 100 are configured to be received through an incision "I" (FIG. 11) or access port (not shown) when in a first or closed configuration (FIG. 1).

Figure 7:
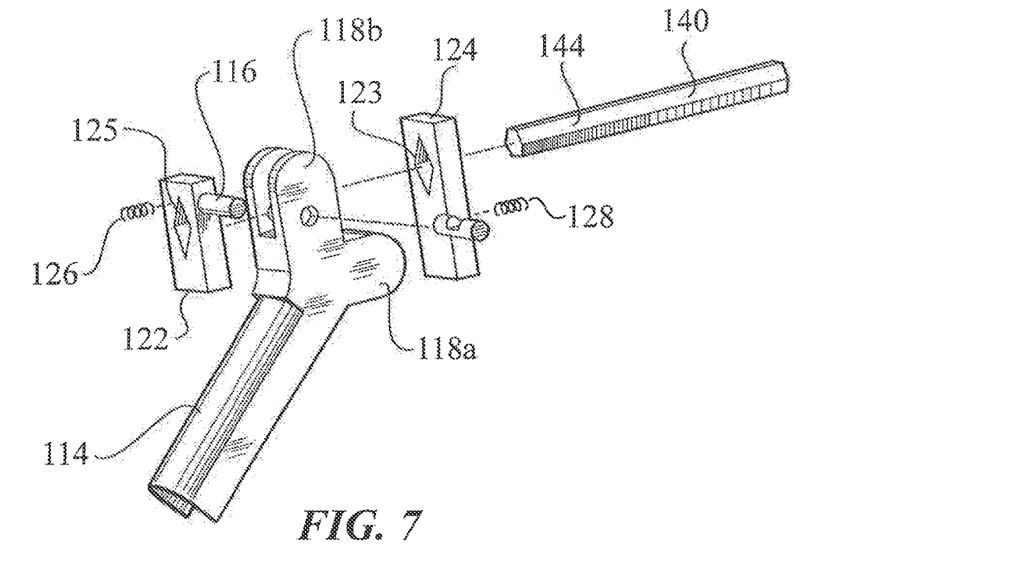
FIG. 7 is an enlarged exploded perspective view of an actuation mechanism according to one embodiment of the present disclosure.
Figure 8:
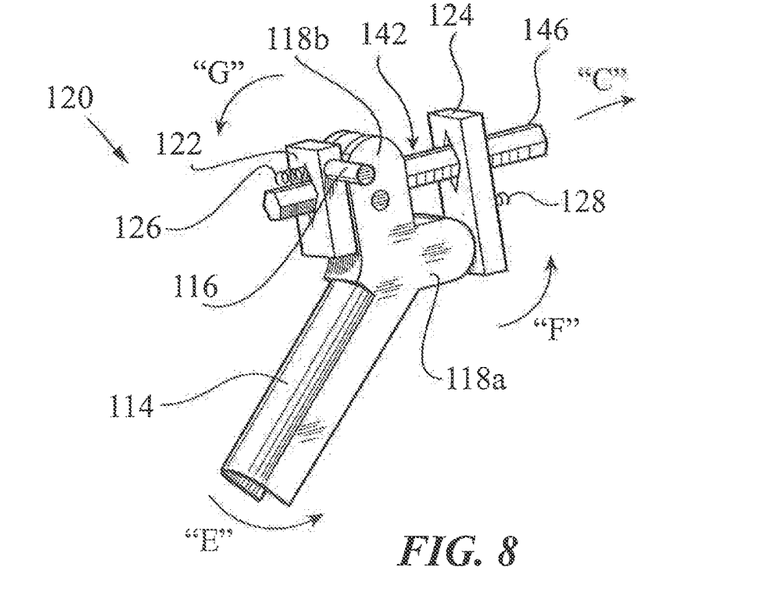
FIG. 8 is an enlarged perspective view of the actuation mechanism of FIG. 7, as assembled for use.

With continued reference to FIGS. 1 and 2, handle assembly 110 includes a fixed handle 112 and a trigger 114. As will be discussed in further detail below, repeated retraction of trigger 114 relative to fixed handle 112 causes closure of capture portion 160. Handle assembly 110 further includes an actuation assembly 120 (FIGS. 7 and 8). As also will be discussed in further detail below, actuation assembly 120 is configured to permit the selective closure of capture portion 160. A release member 116 extends from handle assembly 110 and is configured to permit the opening of capture portion 160.

Figure 3:
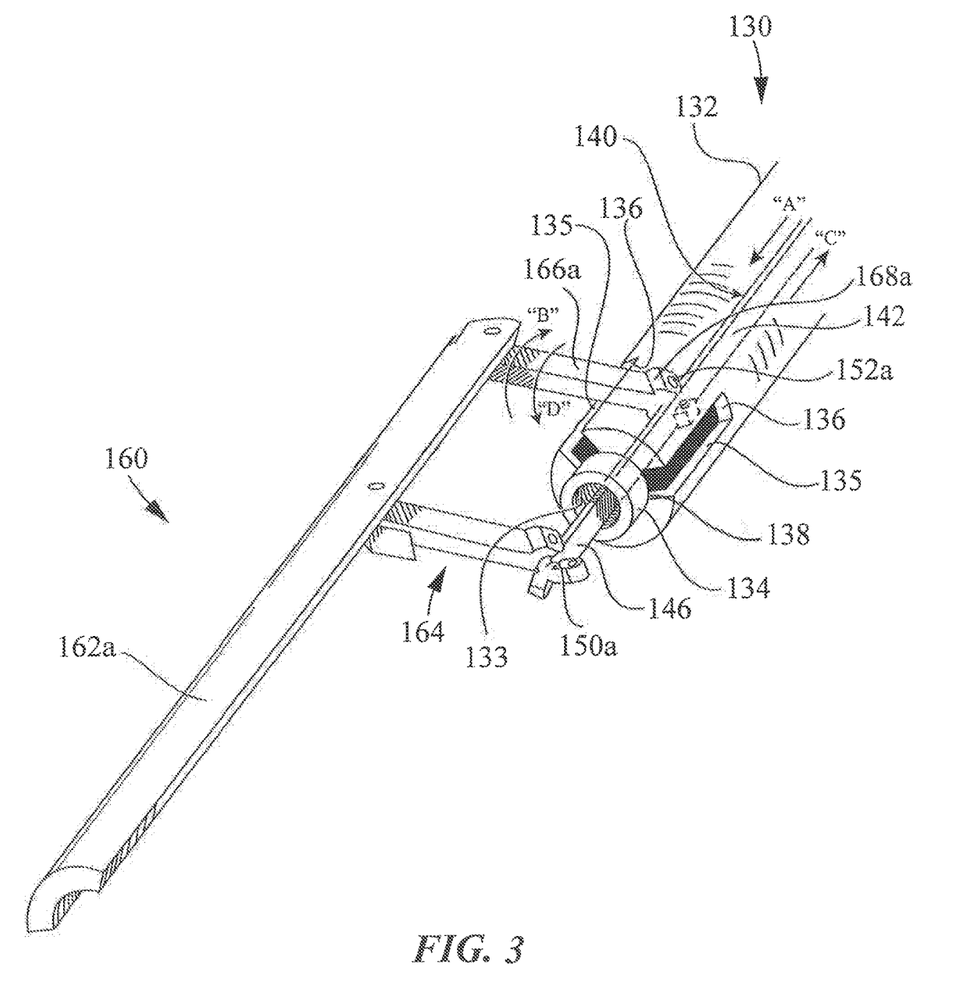
FIG. 3 is an enlarged perspective view of the distal end of the surgical instrument of FIGS. 1 and 2, with two of three linkage assemblies removed to show the operation of the third linkage assembly.

With reference now to FIG. 3, elongated body 130 of surgical instrument 100 includes an outer shaft 132 and an inner shaft 140. Outer shaft 132 includes a substantially cylindrical body defining a longitudinal passageway 133 therethrough configured to receive inner shaft 140. A distal end of outer shaft 132 includes a cylindrical flange 134 and defines a plurality of longitudinal windows or slots 135 extending proximal of cylindrical flange 134. Although shown having three windows 135, as will become apparent below, outer shaft 132 may define only two windows or may include four or more windows. A proximal end of each longitudinal window 135 is formed by a distal facing surface 136 of outer tube 132. A distal end of each longitudinal window 135 is formed by a proximal facing surface 138 of cylindrical flange 134. As will be described in further detail below, distal facing surfaces 136 of outer shaft 132 facilitate the closing of capture portion 160, while proximal facing surfaces 138 of cylindrical flange 134 facilitates opening of capture portion 160.

Figure 4:
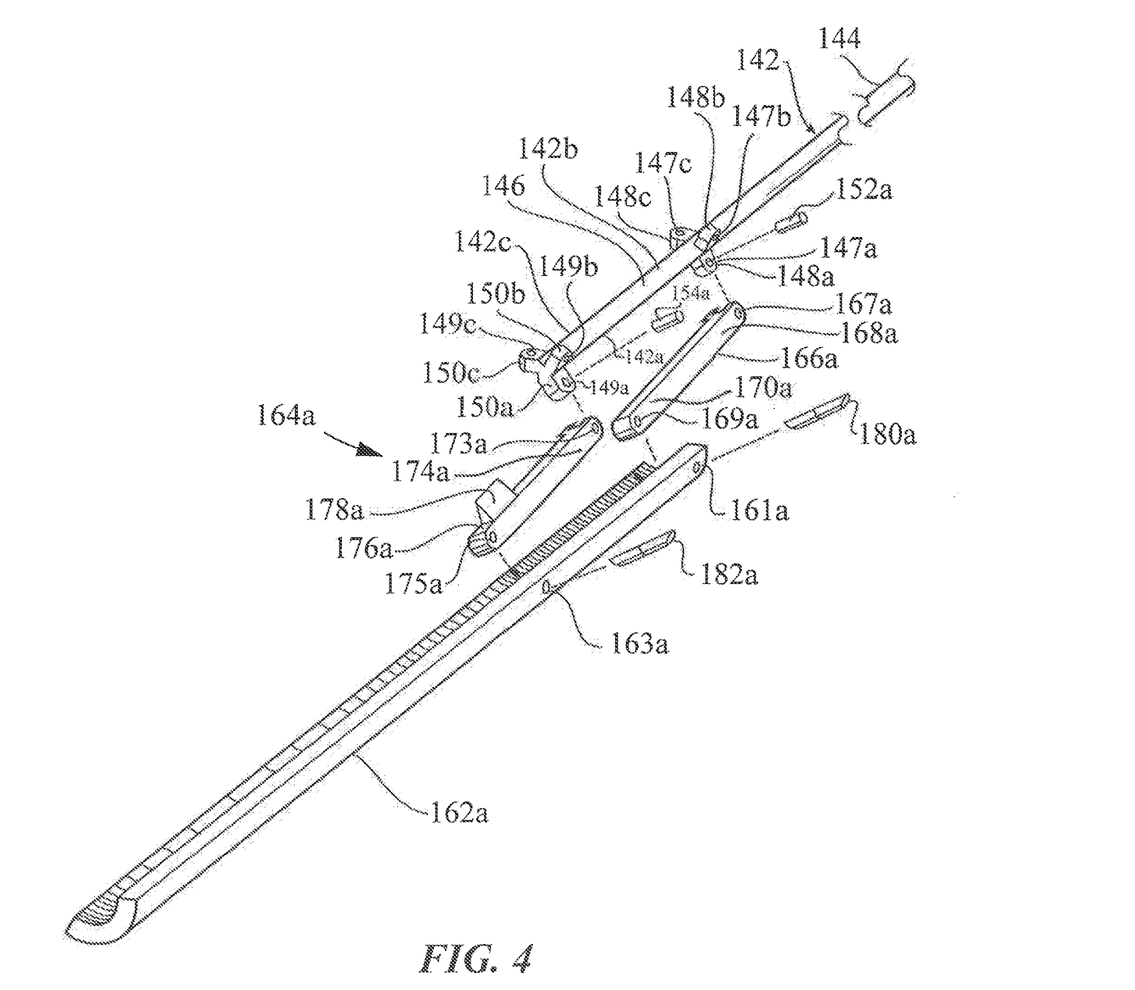
FIG. 4 is an enlarged exploded view of the distal end of the surgical instrument of FIG. 3.
Figure 5:
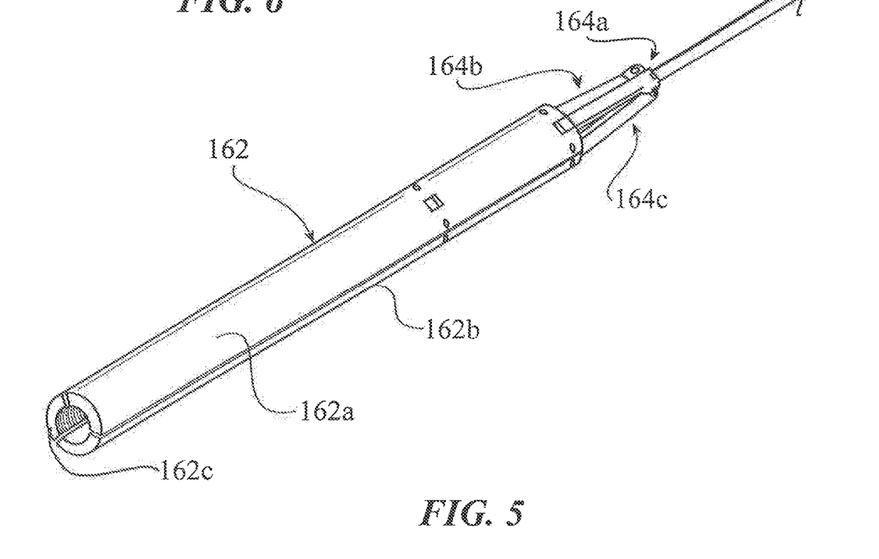
FIG. 5 is perspective view of the capture portion of the surgical instrument of FIGS. 1 and 2, in a first or closed configuration.
Figure 6:
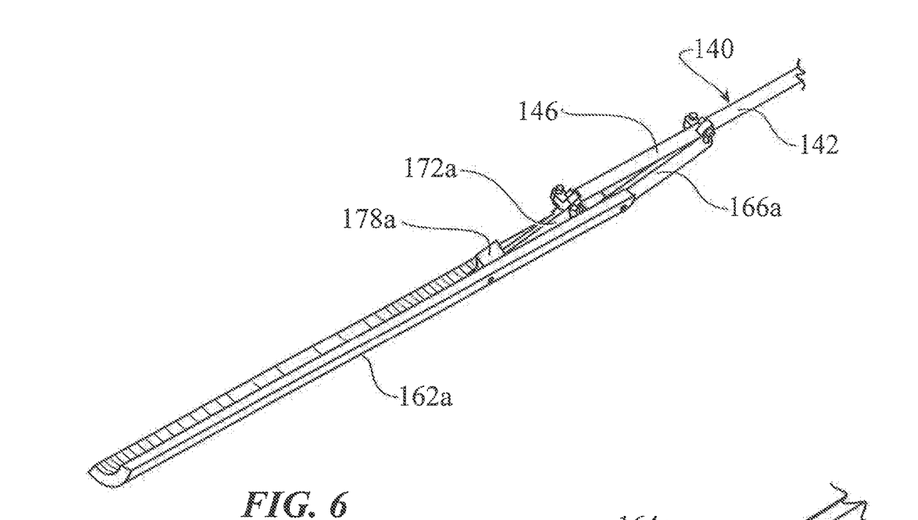
FIG. 6 is a perspective view of a single linkage assembly of the capture portion of the surgical instrument of FIGS. 1 and 2.

With reference now to FIGS. 4-6, inner shaft 140 includes an elongated member 142 having a proximal end 144 operably connected to handle assembly 110 (FIG. 1) and a distal end 146 operably connected to capture portion 160. Inner shaft 140 is configured to reciprocate within outer shaft 132 to effect the operation of capture portion 160. As shown, distal end 146 of elongated member 142 includes a plurality of sides 142a, 142b, 142c, forming a triangular cross-section. As will be discussed in further detail below, the number of sides of elongated member 142 corresponds to the number of longitudinal windows 135 formed in the distal end of outer shaft 132. Each of sides 142a, 142b, 142c of elongated member 142 includes a proximal flange 148a, 148b, 148c spaced proximally of distal end 146 and a distal flange 150a, 150b, 150c formed on distal end 146. Each flange 148a, 148b, 148c, 150a, 150b, 150c defines an opening 147a, 147b, 147c, 149a, 14b, 149c, respectively. Proximal flanges 148a, 148b, 148c and distal flanges 150a, 150b, 150c are each configured for operable connection with capture portion 160.

With continued reference to FIGS. 4-6, capture portion 160 includes a plurality of longitudinal capture sections 162a, 162b, 162c. As shown, capture portion 160 includes three capture sections 162a, 162b, 162c, however, it is envisioned that alternative embodiments of the present disclosure may have as few as two capture sections or four or more capture sections. Capture sections 162a, 162b, 162c are configured to fit together to form a substantially cylindrical body 162 when surgical instrument 100 is in the first or closed condition (FIG. 1). In this manner, capture portion 160 is configured to be received through an incision "I" (FIG. 10) or trocar assembly. Capture portion 160 is further configured such that capture sections 162a, 162b, 162c may be radially spaced apart to form a tissue receiving space 161 therebetween when capture portion 160 is in a second or open condition (FIG. 2).

With reference still to FIGS. 4-6, each of capture sections 162a, 162b, 162c is operably connected to distal end 146 of inner shaft 142 by a linkage assembly 164a, 164b, 164c (FIG. 5). Linkage assemblies 164a, 164b, 164c operate to maintain capture sections 162a, 162b, 162c in parallel relation throughout the opening and closing of capture portion 160. Each of linkage assemblies 164a, 164b, 164c are substantially similar and therefore will only be described as relates to linkage assembly 164a. Linkage assembly 164a includes a proximal linkage member 166a and a distal linkage member 172a. A proximal end 168a of proximal linkage member 166a is configured for pivotal connection with proximal flange 148a of inner shaft 142 and a proximal end 174a of distal linkage member 172a is configured for pivotal connection with distal flange 150a of inner shaft 142. In one embodiment, and as shown, proximal end 168a of proximal linkage member 166a and proximal end 174a of distal linkage member 172a each define an opening 167a, 173a, respectively. A linkage pin 152a is received through opening 147a in proximal flange 148a and opening 167a in proximal end 168a of proximal linkage member 166a and a linkage pin 154a is received through opening 149a in distal flange 150a and opening 173a in proximal end 174a of distal linkage member 172a to pivotally secure proximal end 168a of proximal linkage member 166a and proximal end 174a of distal linkage member 172a, respectively, to distal end 146 of inner shaft 142. Proximal ends 168a, 174a of proximal and distal linkage members 166a, 172a, respectively, may further include a forked configuration, as shown, to reinforce and/or stabilize the pivotal connection between proximal and distal linkage members 166a, 172a, respectively, and distal end 146 of inner shaft 142.

With reference still to FIGS. 4-6, distal ends 170a, 176a of proximal and distal linkage members 166a, 172a, respectively, each define an opening 169a, 175a, respectively. Each of openings 169a, 175a is configured to receive a linkage pin 180a, 182a, respectively. A proximal end of capture section 162a defines a pair of openings 161a, 163a. Proximal linkage member 166a is pivotally secured to capture section 162a when linkage pin 180a is received through opening 169a in distal end 170a of proximal linkage member 166a and through opening 161a in capture section 162a. Similarly, distal linkage member 172a is pivotally secured to capture section 162a when linkage pin 182a is received through opening 175a in distal end 176a of distal linkage member 172a and through opening 163a in capture section 162a.

With reference to FIGS. 3-6, distal linkage member 172a includes a sharpened member 178a on a radially inward facing section thereof when surgical instrument 100 is in the first or closed configuration (FIG. 1). Sharpened member 178a is configured to engage and to cut an incision in a gallbladder or other tissue received within capture portion 160 as capture sections 162a, 162b, 162c are approximated towards one another. Sharpened member 178a is sufficiently angled to cut a gallbladder or other tissue without a large forcing having to be applied by capture portion 160, but is not so sharp as to accidently cut the gallbladder or other tissue through incidental contact and prior to the closing of capture portion 160. In one embodiment, sharpened member 178a may form an angle between ten degrees (10°) and fifty degrees (50°), in another embodiment the angle of sharpened member 178a may be between twenty degrees (20°) and forty degrees (40°), and in yet another embodiment, sharpened member 178a may have an angle of thirty degrees (30°).

With particular reference now to FIG. 3, as shown, linkage assembly 164a operably connects capture section 162a to distal end 146 of inner shaft 142. Distal end 146 of inner shaft 140 extends through cylindrical flange 134 on the distal end of outer shaft 132. Inner shaft 140 is oriented such that proximal flange 148a is aligned with one of windows 135. In this manner, proximal end 168a of proximal linkage member 166a may be received through window 135 and be pivotally connected to proximal flange 148a by linkage pin 152a received through opening 167a (FIG. 4) in proximal end 168a of proximal linkage member 166a and opening 147a in proximal flange 148a. Distal end 170a of proximal linkage member 166a is pivotally secured to capture section 162a by linkage pin 180a received through opening 161a (FIG. 4) in capture section 162a and opening 169a in distal end 170a of proximal linkage member 166a.

With particular reference still to FIGS. 3 and 4, proximal end 174a of distal linkage member 172a is pivotally connected to distal flange 150a on proximal end 146 of inner shaft 140 by linkage pin 154a received through opening 173a in proximal end 174a of distal linkage assembly 172a and opening 149a in distal flange 150a. Distal end 176a of distal linkage member 172a is pivotally secured to capture section 162a by linkage pin 182a received through opening 163a in capture section 162a and opening 175a in distal end 176a of distal linkage member 172a.

Still referring to FIGS. 3 and 4, the operation of capture portion 160 will now be described with reference to capture section 162a and linkage assembly 164a. During opening of capture portion 160 inner shaft 140 is advanced distally, as indicated by arrow "A" (FIG. 3), to cause pivoting of proximal and distal linkage members 166a, 172a. As inner shaft 140 is advanced distally, proximal linkage member 172a engages proximal facing surface 138 of cylindrical flange 134 forming the distal end of window 135. Engagement of proximal facing surface 138 by proximal linkage member 166a causes proximal linkage member 166a to pivot in a clockwise direction about proximal flange 148a, as indicated by arrow "B" (FIG. 3).

During closing of capture portion 160, inner shaft 142 is retracted proximally, as indicated by arrow "C" (FIG. 3). As inner shaft 142 is retracted proximally, proximal linkage member 172a engages distal facing surface 136 of outer shaft 132 forming the proximal end of window 135. Engagement of distal facing surface 136 by proximal linkage member 166a causes proximal linkage member 166a to pivot in a counter-clockwise direction about proximal flange 148a, as indicated by arrow "D". As discussed above, linkage assembly 164a is configured such that capture section 162a is maintained parallel to elongated body 130 throughout the opening and closing of capture portion 160.

With reference now to FIGS. 7 and 8, an actuation assembly 120 for controlling the opening and closing of capture portion 160 is shown. Actuation assembly 120 includes trigger 114, a first plate 122, a second plate 124, a first spring 126 for biasing first plate 122 proximally and a second spring 128 for biasing second plate 124 distally. Trigger 114 includes a horizontal extension 118a and a vertical extension 118b. Horizontal extension 118a is configured to press against second plate 124 when trigger 114 is squeezed. Vertical extension 118b is configured to press against first plate 122 when trigger 114 is squeezed. Each of first and second plates 122, 124 define a diamond-shaped opening 123, 125 for receiving proximal end 144 of inner shaft 140. As shown, proximal end 144 of inner shaft 140 includes a substantially hexagonal longitudinal cross-section configured for selective engagement within openings 123, 125 of first and second plates 122, 124, respectively.

With particular reference now to FIG. 8, squeezing of trigger 114, as indicated by arrow "E" causes proximal retraction of inner shaft 140, as indicated by arrow "C". First plate 122 is inclined relative to inner shaft 140 due to the force from first spring 126. The friction force between inner shaft 140 and first plate 122 prevents inner shaft 140 from advancing distally as the inclined angle of first plate 122 increases the friction force between inner shaft 140 and first plate 122. In this manner, to permit distal advancement of inner shaft 140, first plate 122 must be pulled counter-clockwise, as indicated by arrow "G". As trigger 114 is squeezed, horizontal extension 118a engages second plate 124, causing second plate 124 to pivot counter-clockwise, as indicated by arrow "F". The engagement of second plate 124 with inner shaft 140 causes proximal retraction of inner shaft 140 as second plate 124 is pivoted. Engagement of vertical extension 118b of trigger 114 as trigger 114 is squeezed causes first plate 122 to pivot counter-clockwise, as indicated by arrow "G". As noted above, counter-clockwise movement of first plate 122 reduces the friction force between first plate 122 and inner shaft 140, thereby permitting distal advancement by inner shaft 140.

After the surgeon releases the trigger 114, second spring 128 pushes second plate 124 to its original position, thereby also returning trigger 114 to its original position. First spring 126 pushes first plate 122 back to an initial position, thereby increasing the friction force between first plate 122 and inner shaft 140 to prevent distal advancement of inner shaft 140. Actuation assembly 120 may be configured such that closing of capture portion 160 requires that trigger 114 be squeezed only a single time. Alternatively, the closure of capture portion 160 may require repeated squeezing of trigger 114. In one embodiment, actuation assembly 120 is configured such that complete closure of capture portion 160 requires that trigger 114 is squeezed three times. In this manner, capture portion 160 may be incrementally closed about a gallbladder or other tissue. In some embodiments, inner shaft 140 is biased in the distal direction by a spring (not shown), to cause the opening of capture portion 160 when inner shaft 140 is not prevented from movement by first plate 122.

Figure 9:
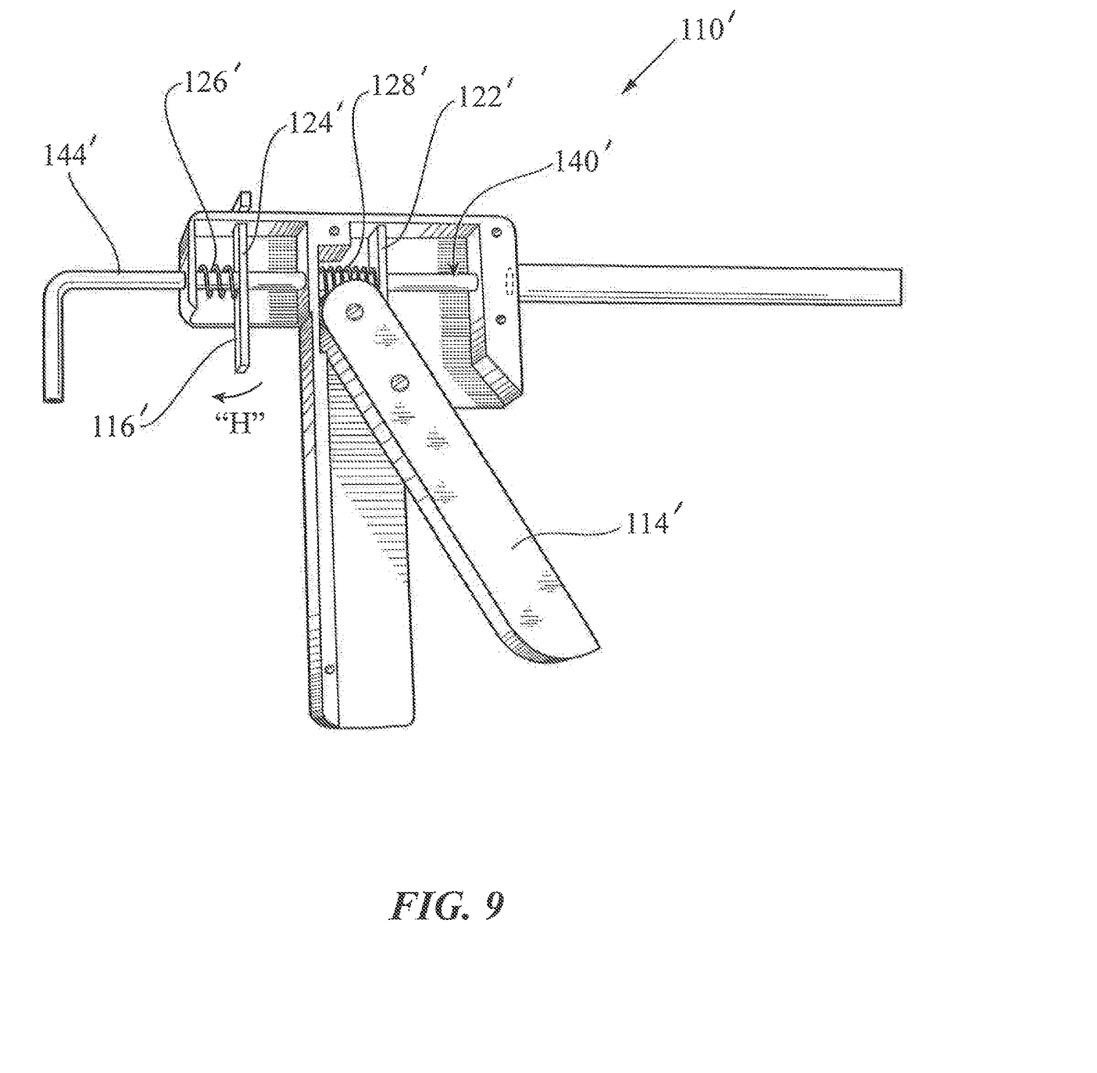
FIG. 9 is an enlarged cut-away side view of a handle assembly including an actuation mechanism according to an alternative embodiment of the present disclosure.

With reference now to FIG. 9, an alternative embodiment of actuation assembly according to the present disclosure is shown generally as actuation assembly 120'. Actuation assembly 120' is substantially similar to actuation assembly 120 and will be described with regard thereto. Actuation assembly 120' includes a proximal plate 122', a distal plate 124', a first spring 126' and a second spring 128'. Each of proximal and distal plates 122', 124' define an opening (not shown) for receipt of a proximal end 144' of an inner shaft 142'. First plate 122' operates in a manner similar to second plate 124 of actuation assembly 120. Squeezing of trigger 114' causes first plate 122' to pivot, thereby retracting inner shaft 140' proximally. Second plate 124' operates in a manner similar to first plate 122 of actuation assembly 120. Second plate 124' engages inner shaft 140' to prevent distal advancement of inner shaft 140'. Clockwise movement of second plate 124', as indicated by arrow "H", causes the release of inner shaft 140'. Inner shaft 140' may be biased distally by a spring (not shown) to open capture portion 160 (FIG. 1) when inner shaft 140' is not prevented from advancing distally by second plate 124'. Alternatively, a surgeon may advance inner shaft 140' distally by pushing on proximal end 144' of inner shaft 140' while maintaining second plate 124' in a release position.

Figure 10:
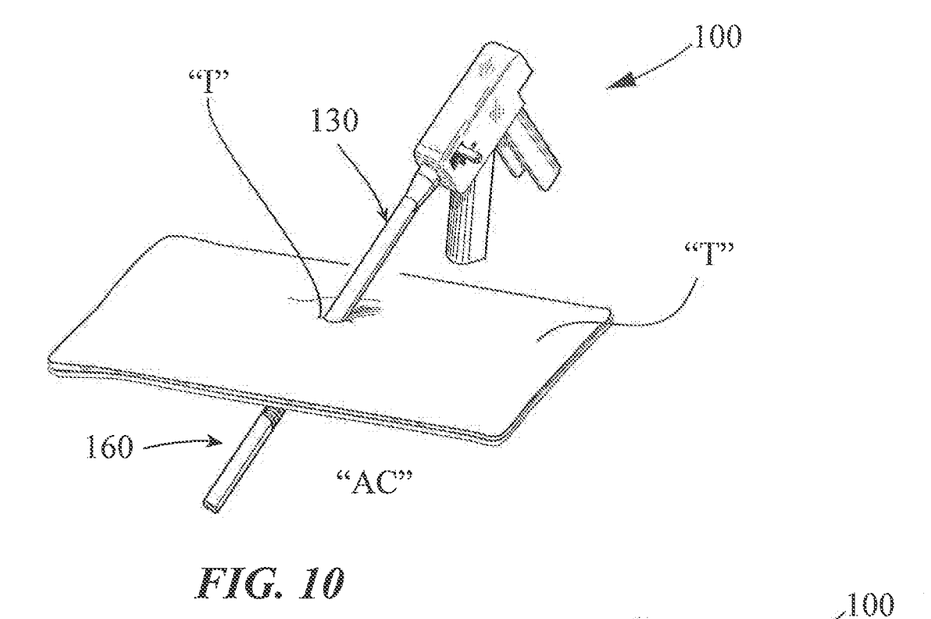
FIGS. 10-13 are perspective views of the surgical instrument in FIGS. 1 and 2 in use during a gallbladder removal procedure.

The use of surgical instrument 100 for the removal of a gallbladder or other tissue within the abdominal cavity will now be described with reference to FIGS. 10-13. Referring initially to FIG. 10, an incision "I" is cut in tissue "T" to access the abdominal cavity "AC" of a patient. As discussed above, elongated body 130 and capture portion 160 are configured to be received through incision "I" or through a trocar assembly (not shown). Capture portion 160 of surgical instrument 100 is then directed through incision "I".

Figure 11:
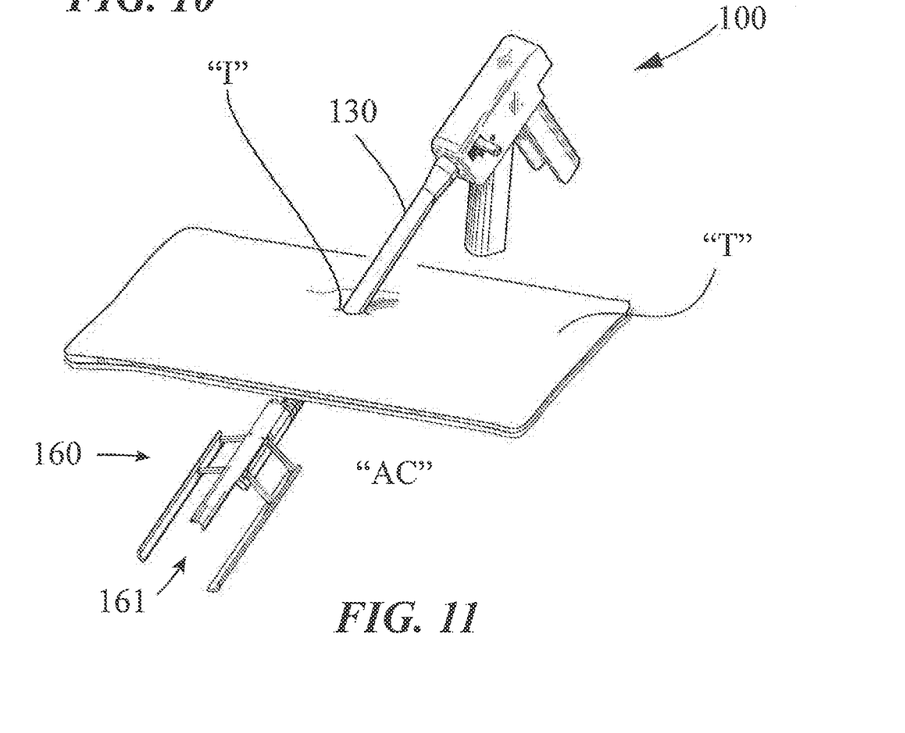

Turning to FIG. 11, once capture portion 160 has been received within abdominal cavity "AC", handle assembly 110 is actuated to cause the opening of capture portion 160. This is accomplished by pressing release member 116 in a counter clockwise motion to disengage first plate 122 (FIG. 8) from inner shaft 140, thereby permitting distal advancement of inner shaft 140 and opening of capture portion 160. As discussed above, inner shaft 140 may be distally biased by a spring or other mechanism (not shown) such that capture portion 160 opens upon pressing of release member 116.

Figures 12, 13:
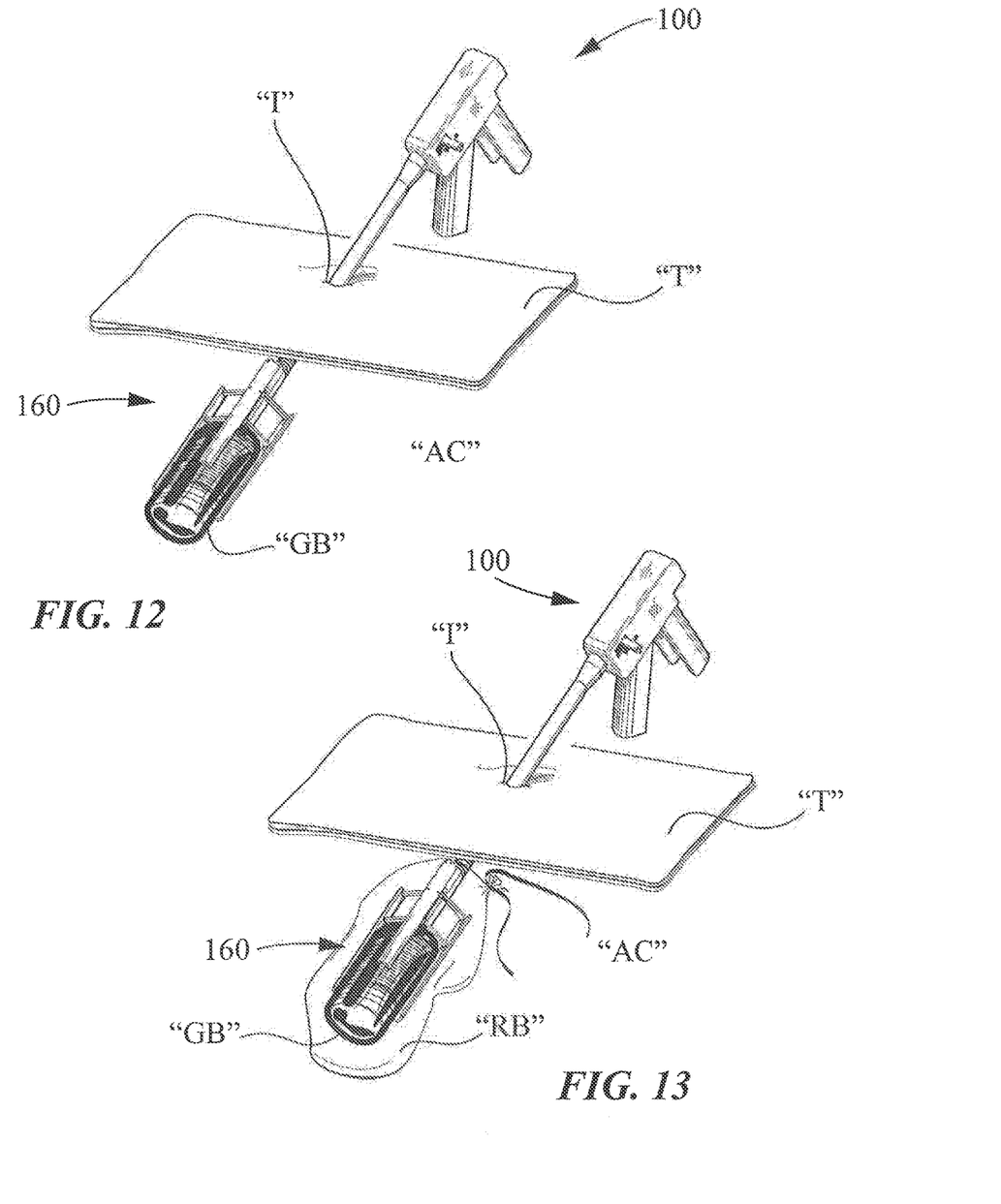

With reference now to FIG. 12, after opening capture portion 160, a gallbladder "GB" or other tissue may be received within tissue receiving space 161 between capture sections 162a, 162b, 162c of capture portion 160. In some embodiments, trigger 114 may be squeezed one or more times to reduce the size of tissue receiving space 161 to accommodate gallbladders "GB" and other tissue of different sizes.

Turning to FIG. 13, once gallbladder "GB" or other tissue has been securely received within tissue receiving space 161 of capture portion 160, a retrieval bag "RB" or other suitable container is placed about capture portion 160. Retrieval bag "RB" is then securely closed to prevent the leakage of bile, stones or other tissue. Trigger 114 may then be further squeezed to cause the closure of capture portion 160, thereby compressing gallbladder "GB". As capture portion 160 moves to a closed configuration, sharpened members 178 formed on each of distal linkage members 172 engage and cut gallbladder "GB" to permit the bile and/or stones contained within gallbladder "GB" to drain into retrieval bag "RB". Once capture portion 160 achieves a closed position, capture portion 160, including retrieval bag "RB" and gallbladder "GB", may be removed through incision "I". Incision "I" may then be closed in a traditional manner.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, it is envisioned that the gallbladder may be received within a retrieval bag prior to being received within capture portion 160. In this manner, sharpened members 178 of capture portion 160 are dulled to prevent cutting of the retrieval bag and the gall bladder is burst during closure of capture portion 160.

The invention claimed is:

1. A surgical instrument comprising:
    a handle;
    an elongated body portion extending distally from the handle;
    a capture portion operably supported on the elongated body portion, the capture portion including at least three capture sections, each capture section including a linkage assembly configured to move the at least three capture sections between an open configuration and a closed configuration, wherein the capture portion includes at least one sharpened member on a first capture section of the at least three capture sections, the at least one sharpened member being formed directly on the linkage assembly of the first capture section, the at least one sharpened member extending radially inwardly from the linkage assembly of the first capture section when the at least three capture sections are in the closed configuration, the at least one sharpened member configured for cutting tissue received within the capture portion when the at least three capture sections are in the closed configuration.

2. The surgical instrument of claim 1, wherein the at least three capture sections form a longitudinal cylinder when the at least three capture sections are in the closed configuration.

3. The surgical instrument of claim 1, wherein each of the linkage assemblies includes a proximal linkage member and a distal linkage member.

4. The surgical instrument of claim 3, further including an inner shaft extending between the handle and the capture portion, wherein each of the proximal and distal linkage members are operably connected to the inner shaft.

5. The surgical instrument of claim 1, wherein the handle includes a trigger for closing the at least three capture sections.

6. The surgical instrument of claim 5, wherein the handle is configured for opening the at least three capture sections.

7. The surgical instrument of claim 1, wherein the at least one sharpened member defines an angle from ten degrees to fifty degrees.

8. The surgical instrument of claim 7, wherein the at least one sharpened member defines an angle of thirty degrees.

9. The surgical instrument of claim 1, wherein the capture portion defines a tissue receiving opening.

10. The surgical instrument of claim 9, wherein the at least one sharpened member is disposed within the tissue receiving opening.

11. The surgical instrument of claim 1, wherein the at least three capture sections extend parallel to one another and define a tissue receiving opening, the tissue receiving opening having a first dimension when the at least three capture sections are in the open configuration and a second dimension when the at least three capture sections are in the closed configuration.

12. The surgical instrument of claim 11, wherein the first dimension is larger than the second dimension.

13. The surgical instrument of claim 1, the at least three capture sections are configured to remain parallel to one another as the at least three capture sections move between the open configuration and the closed configuration.

14. The surgical instrument of claim 1, wherein the at least three capture sections are configured for receipt through an incision when in the closed configuration.

15. The surgical instrument of claim 1, wherein each linkage assembly includes a proximal linkage member and a distal linkage member, the at least one sharpened member being formed on the distal linkage member of the linkage assembly of the first capture section.

* * * * *